US008277448B2

(12) United States Patent
Daluiski et al.

(10) Patent No.: US 8,277,448 B2
(45) Date of Patent: Oct. 2, 2012

(54) EXTERNAL FIXATION (75) Inventors: Aaron Daluiski, New York, NY (US);
Virak Tan, Murray Hill, NJ (US)

(73) Assignee: Wright Medical Technology, Inc.,
Arlington, TN (US)

( * ) Notice: Subject to any disclaimer, the term of this patent is extended or adjusted under 35 U.S.C. 154(b) by 1101 days.

(21) Appl. No.: 11/683,418

(22) Filed: Mar. 7, 2007

(65) Prior Publication Data
US 2008/0221571 A1 Sep. 11, 2008

(51) Int. Cl.
*A61B 17/64* (2006.01)
(52) U.S. Cl. .......................................... 606/54; 606/59
(58) Field of Classification Search ............... 606/53–59, 606/261, 279; 403/385, 389, 391, 396, 400
See application file for complete search history.

(56) References Cited

U.S. PATENT DOCUMENTS

| | | | | |
|---|---|---|---|---|
| 4,365,624 A * | 12/1982 | Jaquet | | 606/56 |
| 4,393,868 A | 7/1983 | Teague | | |
| 4,604,997 A * | 8/1986 | De Bastiani et al. | | 606/55 |
| 4,611,586 A | 9/1986 | Agee et al. | | |
| 4,620,533 A * | 11/1986 | Mears | | 606/54 |
| 4,628,919 A | 12/1986 | Clyburn | | |
| 4,895,141 A | 1/1990 | Koeneman et al. | | |
| 4,920,959 A | 5/1990 | Witzel et al. | | |
| 4,922,896 A | 5/1990 | Agee et al. | | |
| 4,978,347 A | 12/1990 | Ilizarov et al. | | |
| 5,067,954 A * | 11/1991 | Ilizarov | | 606/58 |
| 5,108,394 A * | 4/1992 | Kurokawa et al. | | 606/59 |
| 5,320,622 A * | 6/1994 | Faccioli et al. | | 606/58 |
| 5,397,322 A * | 3/1995 | Campopiano | | 606/57 |
| 5,437,667 A * | 8/1995 | Papierski et al. | | 606/55 |
| 5,527,309 A | 6/1996 | Shelton | | |
| 5,571,103 A | 11/1996 | Bailey | | |
| 5,591,169 A | 1/1997 | Benoist | | |
| 5,658,283 A | 8/1997 | Huebner | | |
| 5,662,649 A | 9/1997 | Huebner | | |
| 5,683,389 A | 11/1997 | Orsak | | |
| 5,741,251 A | 4/1998 | Benoist | | |
| 5,743,898 A * | 4/1998 | Bailey et al. | | 606/54 |
| 5,752,954 A | 5/1998 | Mata et al. | | |
| 5,810,814 A * | 9/1998 | Newson | | 606/59 |
| 5,891,144 A | 4/1999 | Mata et al. | | |
| 5,941,879 A | 8/1999 | Walulik et al. | | |

(Continued)

FOREIGN PATENT DOCUMENTS

| | | |
|---|---|---|
| WO | WO-85/03449 | 8/1985 |
| WO | WO-98/12975 | 4/1998 |

OTHER PUBLICATIONS

Gradl, et al.; "Fractures of the Distal Radius Treated With a Nonbridging External Fixation Technique Using Multiplanar K-Wires"; *The Journal of Hand Surgery*; 2005; 30A: pp. 960-968.

(Continued)

*Primary Examiner* — Eduardo C Robert
*Assistant Examiner* — Jerry Cumberledge
(74) *Attorney, Agent, or Firm* — Duane Morris LLP (57) ABSTRACT

An orthopedic external fixation system may include a distal bar having a curvature that varies along its length, an uncurved proximal bar, a plurality of proximal embedding members, and a plurality of distal embedding members. The proximal and the distal embedding members, sized and shaped for embedding in bone, may attach directly or indirectly to the proximal bar and the distal bar, respectively.

34 Claims, 7 Drawing Sheets

U.S. PATENT DOCUMENTS

| | | | |
|---|---|---|---|
| 6,001,097 A * | 12/1999 | Campopiano et al. | 606/57 |
| 6,053,915 A * | 4/2000 | Bruchmann | 606/54 |
| 6,283,964 B1 | 9/2001 | Weiner | |
| 6,328,737 B1 | 12/2001 | Moorcroft et al. | |
| 6,428,540 B1 * | 8/2002 | Claes et al. | 606/53 |
| 6,527,775 B1 | 3/2003 | Warburton | |
| 6,629,976 B1 | 10/2003 | Gnos et al. | |
| 6,716,212 B1 * | 4/2004 | Pickens | 606/54 |
| 6,793,655 B2 | 9/2004 | Orsak | |
| 6,866,665 B2 | 3/2005 | Orbay | |
| 2003/0109879 A1 * | 6/2003 | Orsak | 606/57 |
| 2003/0149429 A1 | 8/2003 | Ferrante et al. | |
| 2004/0133200 A1 * | 7/2004 | Ruch et al. | 606/54 |
| 2005/0043730 A1 * | 2/2005 | Janowski et al. | 606/56 |
| 2006/0235383 A1 * | 10/2006 | Hollawell | 606/54 |

OTHER PUBLICATIONS

Synthes (USA), "External Fixation" (2000).

International Search Report for PCT/US2008/056001.

Written Opinion for PCT/US2008/056001.

Department of Health & Human Services, R & R External Fixation System, "Single/multiple component metallic bone fixation appliances and accessories", Sep. 6, 2005, 2 pages.

Division of General, Restorative, and Neurological Devices, Indications for Use, 510(k) Summary R & R External Fixator System, Jul. 20, 2005, 4 pages.

FDA>CDHR>510(k) Premarket Notification Database Search, http://www.accessdata.fda.gov/scripts/cdrh/cfdocs/cfPMN/pmn.cfm?ID=86480, 510(k) Premarket Notification Database, Jun. 30, 2005, 3 pages.

EBI—Products, http://www.ebimedical.com/products/detail.cfm?p=090607, MiniFixator and MiniLengthener, Jul. 18, 2005, 4 pages.

Acumed—Small Bone External Fixation System, http://www.acumed.net/product-detail.php?productID=35, Jul. 18, 2005, 4 pages.

* cited by examiner

FIG. 12

EXTERNAL FIXATION

SUMMARY

An orthopedic external fixation system may include a distal bar having a curvature that varies along its length, an uncurved proximal bar, a plurality of proximal embedding members, and a plurality of distal embedding members. The proximal and the distal embedding members, sized and shaped for embedding in bone, may attach directly or indirectly to the proximal bar and the distal bar, respectively.

DETAILED DESCRIPTION

An external fixation system is used to stabilize fractured bone fragments in a relative alignment that facilitates bone healing. An external fixation system typically includes a number of pins, wires, and/or screws percutaneously inserted into bone fragments and clamped to one or more anchoring bars or rods. In the case of nonbridging external fixation of a distal radius fracture, a proximal bar may be fixed to the radius proximal to the fracture by threaded pins or screws, and a distal bar may be fixed to one or more fragments of the radius, distal to the fracture, by K-wires. The distal bar, or a portion thereof, may be curved, as described in more detail below. Fracture stability is achieved by insertion of K-wires, along one or more planes, into the distal bone fragment(s) and attaching the K-wires to the distal bar. The distal bar is then connected to the proximal bar.

Figure 1:
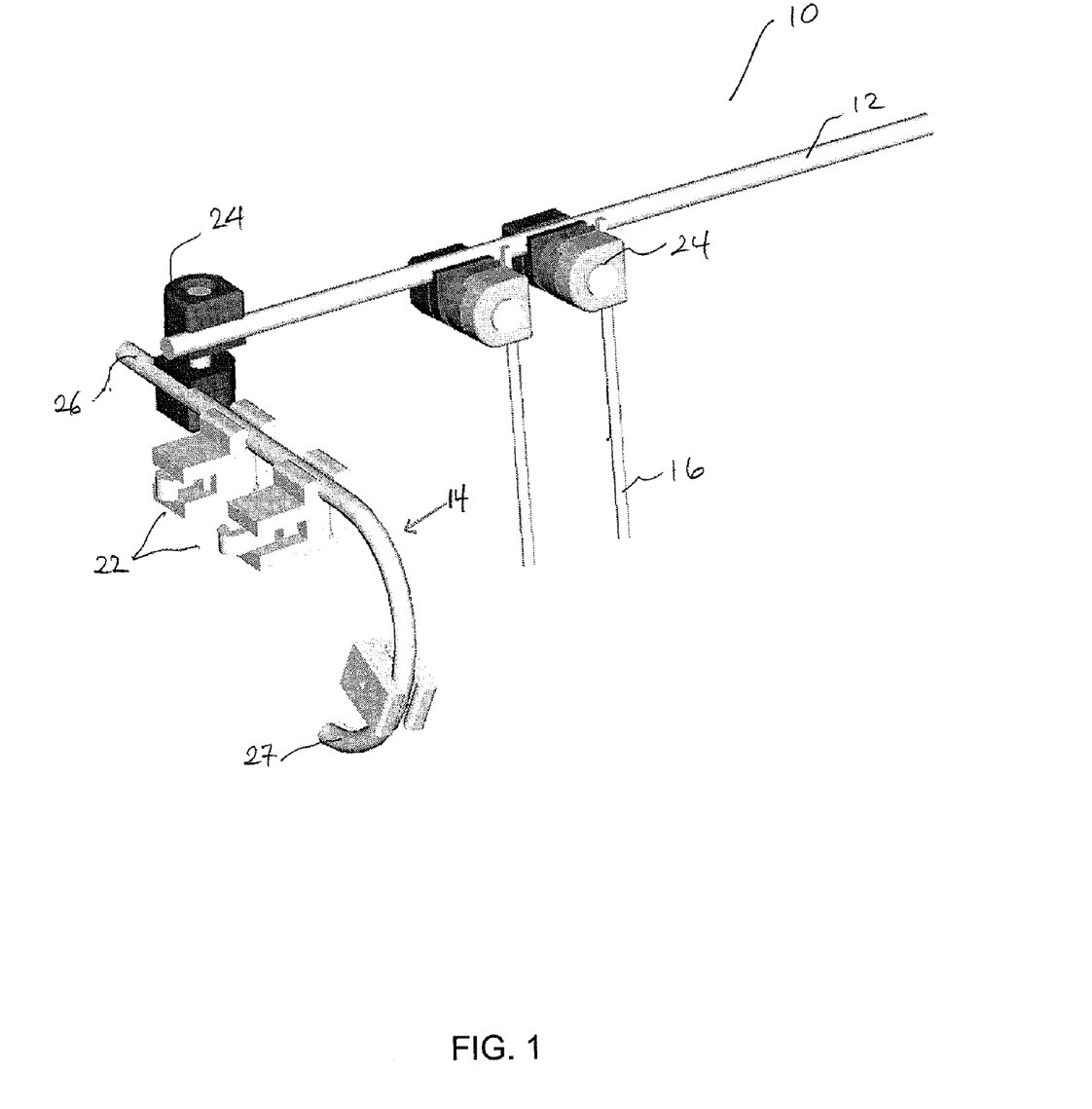
FIG. 1 depicts a perspective view of an embodiment of an external fixation system.

FIG. 1 shows a perspective view of an external fixation system 10 having a distal bar 14, an uncurved proximal bar 12, and a plurality of proximal embedding members 16 ("proximal pins") and proximal embedding member connectors 24. A plurality of the proximal pins 16 may be fixed to the arm of a patient and connected to the proximal bar 12 to serve as an anchor for the external fixation system 10. The proximal embedding member connectors 24 may be positioned along the length of the uncurved proximal bar 12 to anchor the proximal pins 16 appropriately. The proximal bar may optionally have detents or other surface features that mate with a proximal embedding member to define preferred connection positions. The proximal embedding member connectors 24 can be clamped at various positions along the length of the proximal pin 16.

A plurality of proximal embedding members 16 may be attachable to the proximal bar 12 directly or indirectly. Direct attachment between the proximal embedding member and the proximal bar may involve the two components making contact with one another. For example, a proximal bar may have holes sized and shaped to receive a proximal embedding member by press-fit. Holes in the proximal bar may be threaded to receive complementary threads on proximal embedding members. Direct attachment may also be accomplished by the proximal bar having a built-in clamp or other mechanisms to connect the proximal embedding member to the proximal bar without the need for an intermediate component. A proximal embedding member may also be glued to a proximal bar for direct attachment.

Indirect attachment between the proximal embedding member 16 and the proximal bar 12 may include an intermediate clamp to which both components are connected. For example, FIG. 1 shows a plurality of a proximal embedding member connectors 24 connecting a proximal embedding members to a proximal bar.

Distal embedding members 23 may be attachable to a distal bar 14 directly or indirectly in the various ways described above for proximal embedding members and a proximal bar.

The proximal bar may be fixed relative to the patient's forearm by attaching it to the radius with at least two pins/screws, typically positioned at least several centimeters apart from one another along the length of the proximal bar. When so attached, the proximal bar is typically oriented so that it runs parallel to the shaft of the radius, with respect to both the pitch of the bar and its medial/lateral skew with respect to the shaft of the radius, but nonparallel orientations, in pitch and/or skew, are also possible.

A proximal embedding member connector 24 may also connect the distal bar 14 to the uncurved proximal bar 12. FIG. 1 is an illustration of one possible attachment point between the distal bar 14 and the proximal uncurved bar 12. The distal bar 14 may be attached at different points along the length of the proximal uncurved bar 12.

The distal bar 14 has an uncurved portion 26 and a curved portion 27 and lies in a plane transverse (such as perpendicular or oblique) to the proximal bar. The curved portion may curve in a plane transverse to the proximal bar. A plurality of distal embedding member connectors 22 may connect and fix distal embedding members (such as K-wires, not shown) to the distal bar. Proximal and distal embedding members may include radioopaque features to facilitate radiographic confirmation of proper placement.

The proximal and distal bars may have a variety of shapes and sizes. It may have a circular cross-section, round cross-section, elliptical cross-section, polygonal cross-section, and/or square cross-section. If the cross-section has flat sides, the edges defining the sides may be rounded. A bar may have a diameter in the range of about 1 mm to about 12 mm, about 3 mm to about 11 mm, about 3 mm, about 4 mm, about 5 mm, about 8 mm, and/or about 11 mm. The diameter of a bar may be constant along the length of the bar or may vary. (If the bar has other than a circular cross-section, the "diameter" refers to the longest segment that can be obtained by joining two points at the edge of the cross-section.) A bar may be solid or hollow inside. A bar may have a length in the range of about 3 cm to about 30 cm.

The proximal and distal bars may be made of a wide variety of materials. The bars may be made, in whole or in part, from carbon fiber, metal, stainless steel, titanium, aluminum (such as grades 6061 and 7075), plastic, polysulfone, polyether sulfone (such as RADEL®-A plastic resin), polyphenylsulfone (such as RADEL®-R plastic resin), among others. A bar may be radiolucent. A bar may be of unitary construction (i.e., is formed from a single piece of material, without any joints or connections) or may be formed by joining two or more pieces together.

The length of the uncurved portion 26 of the distal bar may be in the range of about 4 centimeters to about 6 centimeters. The curved portion 27 of the distal bar may curve through an arc of at least 45 degrees, at least 60 degrees, at least 90 degrees, between about 90 degrees and about 180 degrees, about 180 degrees, and/or at least 180 degrees. The curved portion 27 of the distal bar 14 may have a constant curvature or a nonconstant curvature. A nonconstant curvature may follow a sector of, for example, a noncircular ellipse, a hyperellipse, a hypoellipse, an oval, a parabola, a hyperbola, or an involute, among other shapes. The distal bar 14 may have a first portion having a first curvature and a second portion having a second curvature which is different from the first curvature.

One or more curved portions of the distal bar 14 may follow a sector of a circle. The distal bar 14 may curve through at least ⅛ of the circumference of a circle, at least ⅙ of the circumference of a circle, at least ¼ of the circumference of a circle, between ¼ and ½ of the circumference of a circle, about ½ of the circumference of a circle, and/or at least ½ of the circumference of a circle. The circle that the distal bar curved portion follows may have a radius in the range of about 0.5 inches to about 5 inches, about 1 inch to about 2 inches, about 1 inch, exactly 1 inch, about 1.5 inches, exactly 1.5 inches, about 2 inches, and/or exactly 2 inches.

One or more curved portions of the distal bar 14 may follow the curvature of a noncircular ellipse. The distal bar 14 may follow the curvature of an ellipse having a major axis of about 7 cm in length and a minor axis of about 5 cm in length. The distal bar 14 may follow the curvature of an ellipse having a major axis of about 6 cm in length and a minor axis of about 4 cm in length. Alternatively, the distal bar 14 may follow the curvature of an ellipse having an eccentricity in the range of about 0.5 to about 0.8, about 0.6 to about 0.8, and/or about 0.69 to about 0.75. (Eccentricity of an ellipse is an unitless quantity that indicates deviation from a circular shape and is defined to equal $\sqrt{1-(b^2/a^2)}$, where a and b are the major and minor axes, respectively, of the ellipse. A circle has an eccentricity of zero and a noncircular ellipse has an eccentricity that is greater than zero but less than one. The eccentricity of an ellipse that reasonably approximates the cross-section of a human wrist typically falls in the range of about 0.6 to about 0.8. The eccentricity of an ellipse that reasonably approximates the cross-section of a human finger typically falls in the range of about 0.5 to about 0.6.) The distal bar 14 may curve through at least ⅛ of the circumference of an ellipse, at least ⅙ of the circumference of an ellipse, at least ¼ of the circumference of an ellipse, between ¼ and ½ of the circumference of an ellipse, about ½ of the circumference of an ellipse, and/or at least ½ of the circumference of an ellipse.

The distal bar 14 may be positioned on the skin or with space between it and the patient's skin to allow for postoperative swelling. The distal bar may be spaced apart from the skin at distance in the range of 0 cm to about 3 cm, 0 cm to about 2 cm, 0 cm to about 1.5 cm, about 1 cm to about 1.5 cm, and/or about 0.5 cm to 1.5 cm. For example, the distal bar may be designed to follow a curve appropriately larger than the relevant portion of the patient's anatomy. If no swelling is expected, then a bar that contacts or lies within a few millimeters of the skin may be used to provide a low-profile fixation system.

Figure 2:
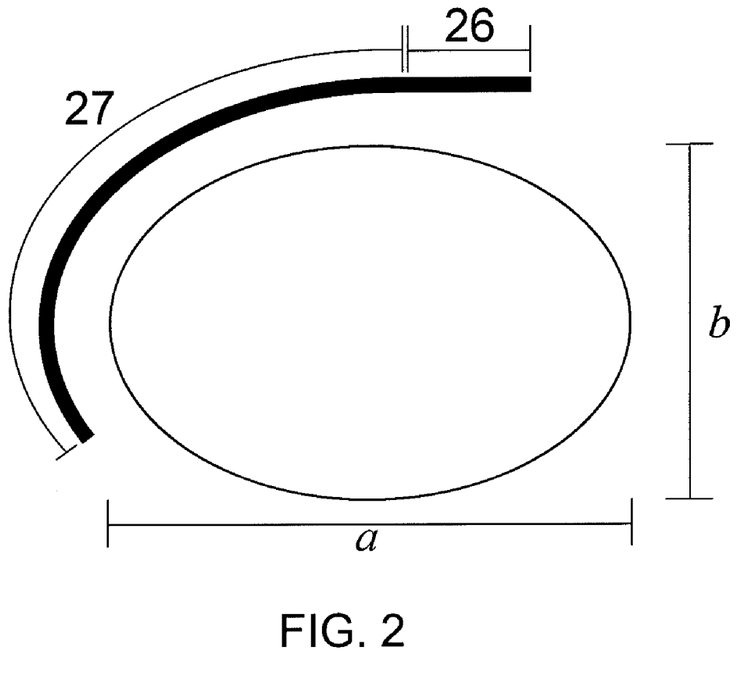
FIG. 2 shows an embodiment of a distal bar having an uncurved portion and a curved portion following the curvature of a noncircular ellipse.

FIG. 2 shows an embodiment of a distal bar. In the depicted embodiment, the distal bar 14 has a curved portion 27 and an uncurved portion 26. The curved portion extends from one end of the uncurved portion and follows an elliptical curve through somewhat more than ¼ of the circumference of the ellipse. The ellipse that the curved portion follows has major and minor axes that exceed the major and minor axes, a and b, respectively, of the depicted ellipse that approximates the cross-section of the anatomy about which the bar is positioned (such as the forearm in the vicinity of the distal radius).

Figure 3:
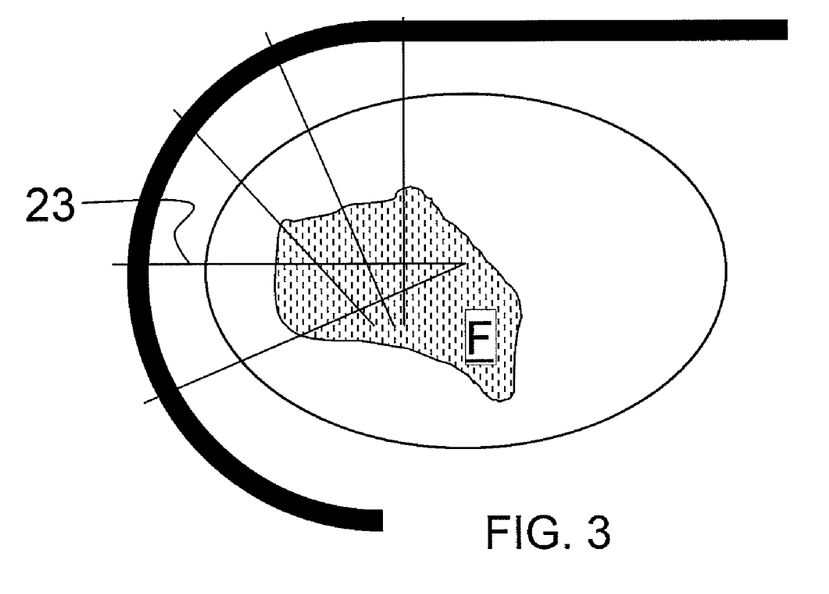
FIG. 3 shows an embodiment of a distal bar having an uncurved portion and a semicircular curved portion, with a plurality of distal embedding members extending from the distal bar into bone.

FIG. 3 depicts another embodiment of a distal bar. In this embodiment, the curved portion has a constant curvature (i.e., it is circular) and curves through an arc of 180 degrees (i.e., it has a semicircular shape). This distal bar may be termed a "J-bar" in view of its shape. FIG. 3 also depicts an exemplary use of the distal bar. Each of a plurality of distal embedding members 23 (such as K-wires) extend from the distal bar into a bone fragment F. The distal embedding members may be so oriented and positioned relative to one another that they form a "subchondral scaffold" of wires that support the fragment in one or more planes. The distal embedding members may also be oriented to cross the fracture lines.

Figure 4:
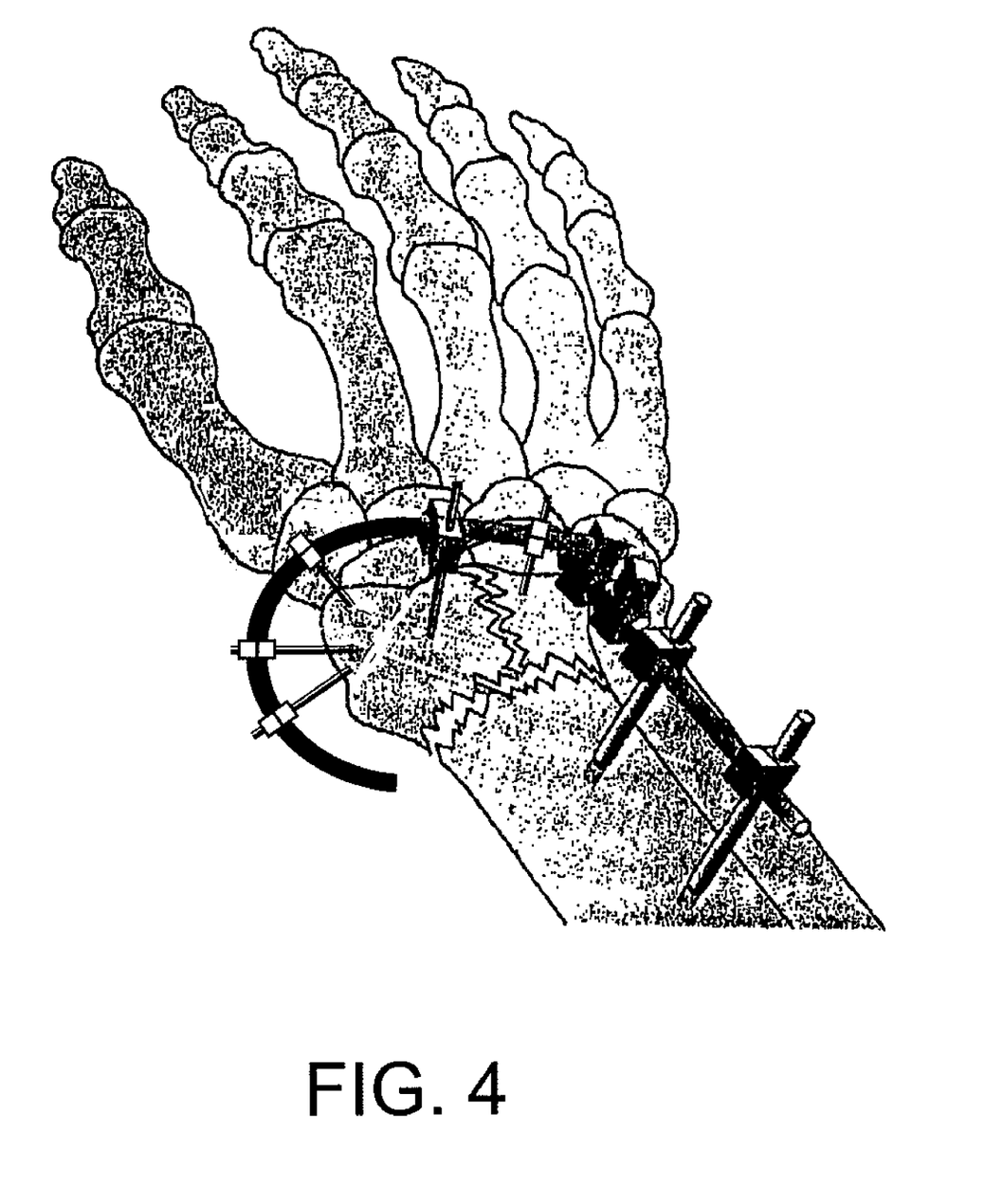
FIG. 4 shows an exemplary use of an embodiment illustrated in FIG. 1 with a plurality of distal embedding members extending from the distal bar into bone.

In one exemplary use shown in FIG. 4, the system is used in the repair of a distal radius fracture. In such a scenario, the curved portion 27 of the distal bar 14 may be sized an shaped so that it wraps around the patient's distal forearm on the radial (anatomically lateral) side. The proximal bar is fixed to the shaft of the radius with pins and connectors. The distal bar is fixed to the proximal bar by a connector. A plurality of K-wires are fixed to the distal bar by connectors and embedded in the distal radius fragments. The curved portion of the distal bar permits placement of the K-wires at a wide variety of angles from several positions around the distal radius without the need to bend or otherwise distort the wires. Using unbent K-wires helps minimize wobble, shift, torque, and shear stress. The K-wires may, however, be bent and still provide enough support if proper placement into the distal fragment requires it.

Figure 5:
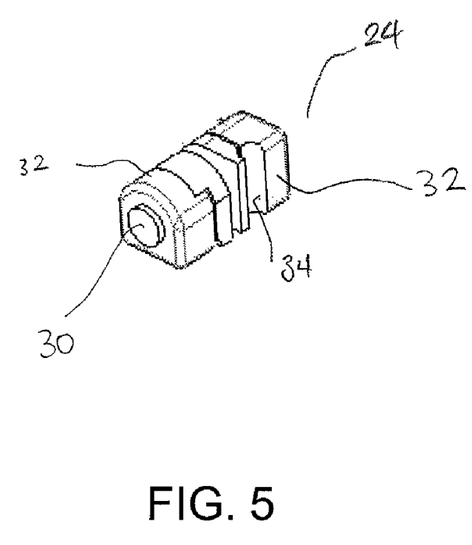
FIGS. 5-6 show perspective view and a side view, respectively, of a proximal embedding member connector.
Figure 6:
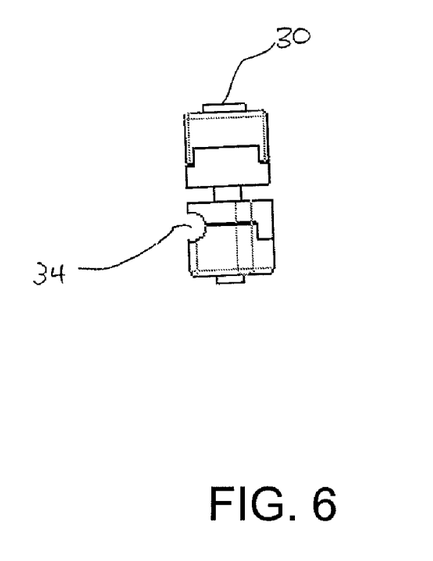

FIGS. 5 and 6 illustrate an embodiment of a proximal embedding member connector 24 having two grooved blocks 32. The blocks may be identical to one another. The block defines a groove, such as C-shaped groove. In the depicted embodiment, the blocks define C-shaped grooves 34 that are oriented perpendicular to one another. The two blocks 32 may be oriented at other angles with respect to each other, so that the grooves 34 may be oriented in a wide range of angles depending on a patient's need. The grooves may be sized and shaped to receive the uncurved proximal bar 12 and/or the proximal pins 16. Once a desired position of the proximal embedding member connectors 24 is obtained, a locking screw 30 may simultaneously lock the two C-groove blocks 32 to each other and fix the locked blocks to the uncurved proximal bar 12 as shown in FIG. 1. By tightening the screw, the clamping force is applied and two blocks 32 will come together until they contact one another. FIG. 6 represents an embodiment of an unlocked configuration of a proximal embedding member connector 24.

Figure 7:
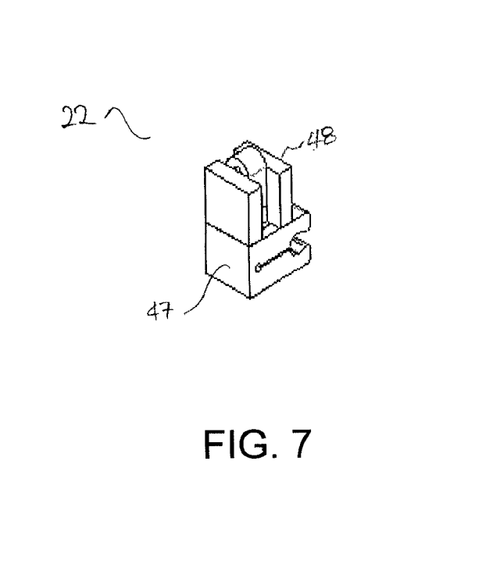
FIGS. 7-9 illustrate perspective, a front view of an unlocked configuration, and a front view of a locked configuration, respectively, of a distal embedding member connector.
Figure 8:
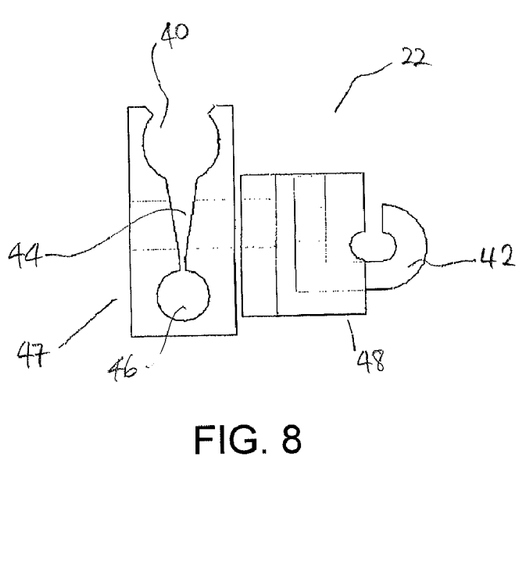
Figure 9:
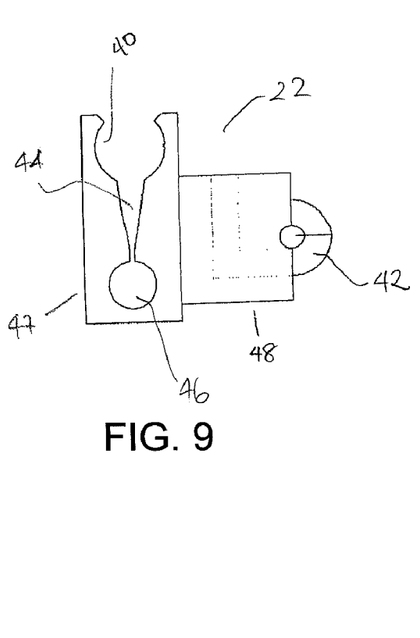

FIGS. 7-9 show various views of an exemplary embodiment of a distal embedding member connector 22. The depicted embodiment includes a C-groove block 47 and J-block 48, each having a groove to receive a distal bar 14 and a distal embedding member 20, respectively. FIG. 8 illustrates the exemplary distal embedding member connector in an unlocked configuration. As for the proximal embedding member connector, a locking screw (not shown) may bring the J-block 48 and the C-groove block 47 until they contact one another to secure the distal embedding member 20 to the distal embedding member connector 22 and fix the position of the distal member connector 22 with respect to the distal bar 14. Distal embedding member connectors 22 may be positioned along the length of the uncurved portion of the distal bar 14 as shown in FIG. 1.

Figure 10:
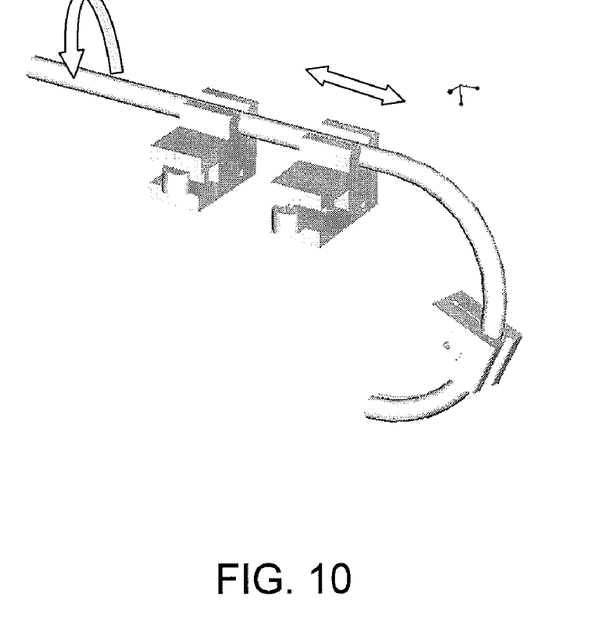
FIG. 10 illustrates connector motions along a distal bar.
Figure 11:
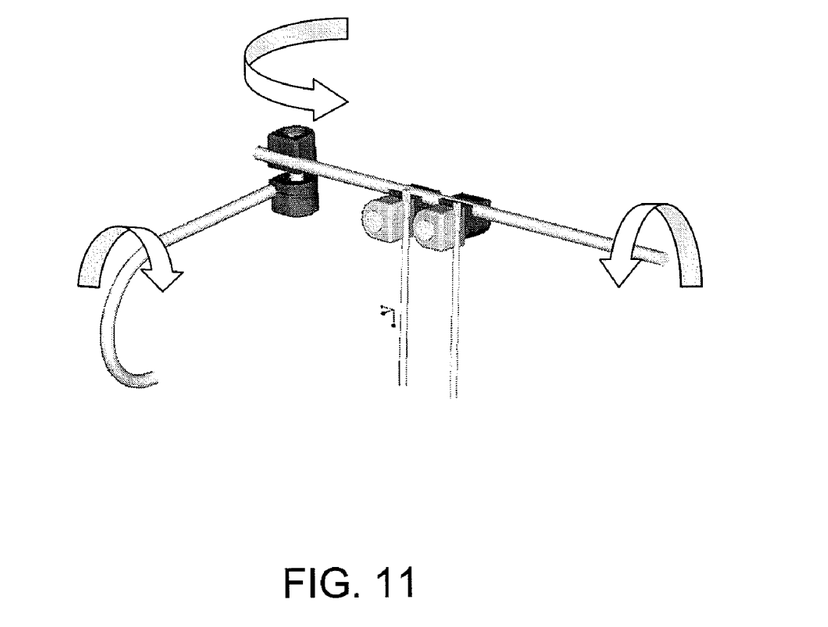
FIG. 11 illustrates various degrees of freedom in an embodiment of an external fixation system.

Distal embedding member connectors 22 may slide and/or rotate along and with respect to the distal bar (FIG. 10) These motions, taken with other possible adjustments (shown in FIG. 11), illustrate the various ways by which the distal bar position and orientation may be controlled.

The C-shaped groove 44 and the through hole 46 may be connected by a v-shaped cutout 44 as shown in FIG. 8. The v-shaped cutout or other similar shapes that have a decreasing width may facilitate clamping of the distal embedding member connector 22 by providing initial resistance to connection that abruptly gives way with a click to provide audible and tactile confirmation of correct positioning.

Some or all portions of the proximal and/or distal embedding member connectors may be made with radiolucent material such as carbon fiber.

Figure 12:
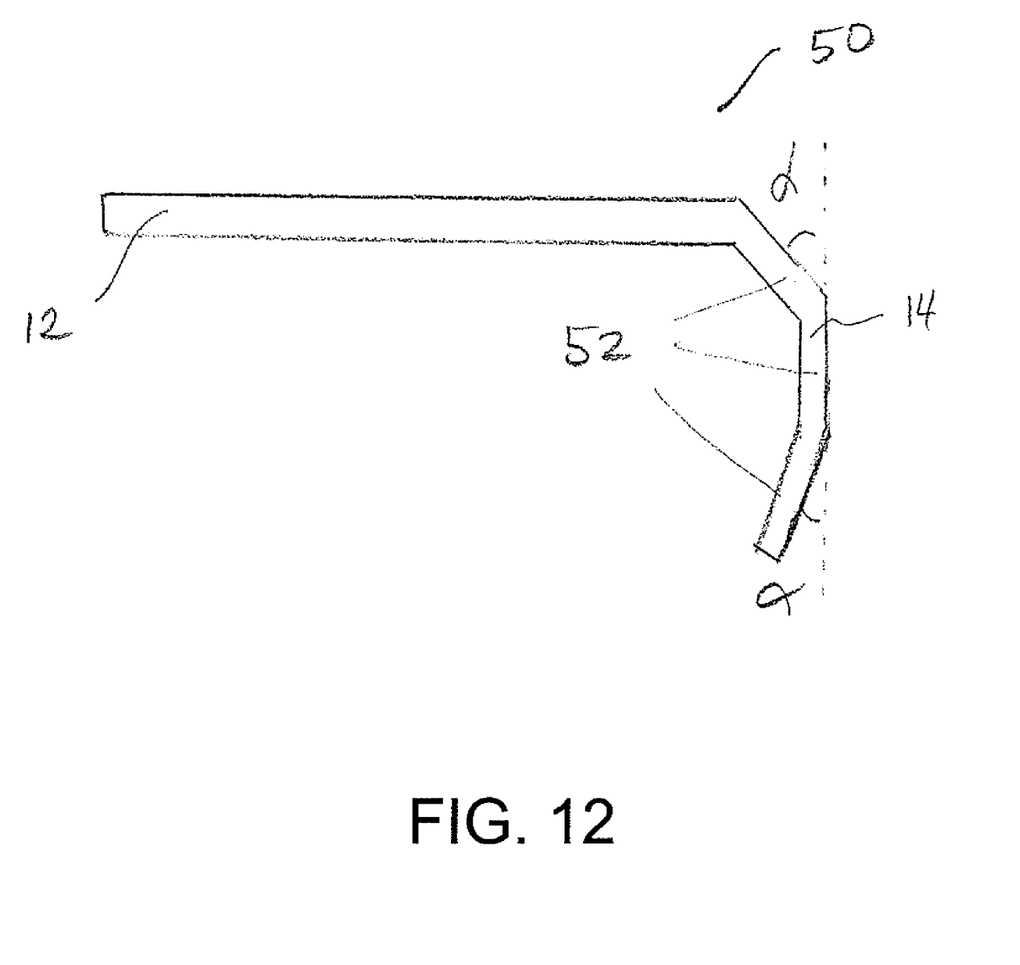
FIG. 12 shows an embodiment with a distal bar having multiple linear segments.

FIG. 12 shows a distal bar 50 for an external fixation system having a plurality of linear segments 52 bent at angles relative to one another. The distal bar 50 may have one, two, three, four, five, six, or more linear segments. Adjacent linear segments 52 may extend relative to one another at an angle α in the range of about 5 degrees to about 20 degrees, separately for each occurrence. The distal embedding member connectors 22 as shown in FIG. 1 may be used in this configuration to secure the distal embedding members 20 to the linear segments 52. In some embodiments, there may be a single linear segment 52 which may extend from the rest of the bar at a variety of angle. If that single linear segment extends at an angle of or about 90 degrees, then the bar may be termed an "L-bar."

As discussed previously, external fixation systems described herein may be used to provide non-bridging fixation for fractures of the distal radius. They may also be used to provide spanning fixation and/or distraction across a distal radius fracture and/or across one or more bones of the carpus. The disclosed external fixation systems may also be used in treating fractures of other bones, such as metacarpals, phalanges in hands or feet, ulna, humerus, clavicle, scapula, the bony pelvis, femur, tibia, fibula, bones of the ankle, and/or metatarsals.

We claim:

1. An external fixation system comprising:
a distal bar having a curvature varying along its length;
an uncurved proximal bar;
a plurality of proximal embedding members attachable directly or indirectly to the proximal bar and sized and shaped for embedding in bone;
a plurality of distal embedding members shaped for embedding in bone; and
at least one distal embedding member connector configured to be coupled to the distal bar, the at least one distal embedding member connector including:
a first block defining a first hole adjacent to a side surface of the first block and a cutout extending along a length of the side surface and connected to the first hole, the cutout having a decreasing width, the first hole sized and configured to receive the distal bar therein,
a second block including a second hole sized and configured to receive one of the plurality of distal embedding members therein, and
a locking screw configured to couple the first block to the second block.

2. The system of claim 1, wherein the distal bar comprises an uncurved portion having zero curvature and a curved portion having nonzero curvature.

3. The system of claim 2, wherein the uncurved portion of the distal bar has a length in the range of about 4 to about 6 centimeters.

4. The system of claim 2, wherein the curved portion of the distal bar curves through an arc of at least 45 degrees.

5. The system of claim 2, wherein the curved portion of the distal bar curves through an arc of at least 60 degrees.

6. The system of claim 2, wherein the curved portion of the distal bar curves through an arc of at least 90 degrees.

7. The system of claim 2, wherein the curved portion of the distal bar curves through an arc of between about 90 degrees and about 180 degrees.

8. The system of claim 2, wherein the curved portion of the distal bar curves through an arc of about 180 degrees.

9. The system of claim 2, wherein the curved portion of the distal bar curves through an arc of at least 180 degrees.

10. The system of claim 2, wherein the curved portion has a constant curvature.

11. The system of claim 2, wherein the curved portion has a nonconstant curvature.

12. The system of claim 1, wherein the distal bar comprises a first portion having a first curvature and a second portion having a second curvature different from the first curvature.

13. The system of claim 1, wherein the distal bar curvature follows the curvature of a noncircular ellipse.

14. The system of claim 13, wherein the distal bar curvature follows the curvature of an ellipse having a major axis of about 7 cm in length and a minor axis of about 5 cm in length.

15. The system of claim 13, wherein the distal bar curvature follows the curvature of an ellipse having an eccentricity in the range of about 0.6 to about 0.8.

16. The system of claim 13, wherein the distal bar curvature follows the curvature of an ellipse having an eccentricity in the range of about 0.69 to about 0.75.

17. The system of claim 13, wherein the distal bar curves through at least ⅛ of the circumference of the ellipse.

18. The system of claim 13, wherein the distal bar curves through at least ⅙ of the circumference of the ellipse.

19. The system of claim 13, wherein the distal bar curves through at least ¼ of the circumference of the ellipse.

20. The system of claim 13, wherein the distal bar curves through between about ¼ and ½ of the circumference of the ellipse.

21. The system of claim 13, wherein the distal bar curves through about ½ of the circumference of the ellipse.

22. The system of claim 13, wherein the distal bar curves through at least ½ of the circumference of the ellipse.

23. The system of claim 1, wherein the distal bar defines a plurality of through holes.

24. The system of claim 1, wherein the distal bar is made at least in part of carbon fiber.

25. The system of claim 1, wherein the distal embedding members comprise K-wires.

26. The system of claim 1, wherein the distal bar includes at least three linear segments.

27. The system of claim 26, wherein adjacent segments are bent at angles in the range of about 5 degrees to about 20 degrees relative to one another.

28. An external fixation method for an anatomic site using the system of claim 1, the method comprising:
embedding the proximal embedding members in a bone proximal to the anatomic site;

attaching the proximal uncurved bar to the proximal embedding members;

attaching the distal bar to the proximal uncurved bar;

attaching the at least one distal embedding member connector to the distal bar;

embedding the distal embedding members in bone at the anatomic site; and attaching the distal embedding members to the distal bar embedding member connector.

29. The method of claim 28, wherein the proximal uncurved bar is so positioned as to span a joint.

30. The method of claim 28, wherein the proximal uncurved bar is so positioned as not to span a joint.

31. The method of claim 30, wherein the proximal embedding members are embedded in a radius shaft, and the distal embedding members are embedded in one or more distal radius fragments.

32. The method of claim 28, wherein:

the proximal uncurved bar, when attached to the proximal embedding members, defines an axis; and the distal bar, when attached to the distal embedding members, curves in a plane transverse to the axis of the proximal uncurved bar.

33. The method of claim 32, wherein the plane of the distal bar is perpendicular or substantially perpendicular to the axis of the proximal uncurved bar.

34. The external fixation system of claim 1, wherein the first block defines a groove having an cylindrical cross-sectional geometry that defines a central axis that is substantially parallel to an axis defined by the first hole, the groove intersecting the side surface of the first block and being connected to the first hole by the cutout.

* * * * *